(12) United States Patent
Brandt et al.

(10) Patent No.: US 8,356,596 B2
(45) Date of Patent: Jan. 22, 2013

(54) DEVICE FOR SUPPLYING A RESPIRATOR WITH BREATHING GAS

(75) Inventors: Andreas Brandt, Lübeck (DE); Thorsten Haase, Lübeck (DE); Ralf Heesch, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 604 days.

(21) Appl. No.: 12/574,996

(22) Filed: Oct. 7, 2009

(65) Prior Publication Data

US 2010/0116273 A1 May 13, 2010

(30) Foreign Application Priority Data

Nov. 13, 2008 (DE) .................. 10 2008 057 180

(51) Int. Cl.
*A62B 7/00* (2006.01)
*A62B 9/00* (2006.01)
*A61M 16/00* (2006.01)

(52) U.S. Cl. ......... 128/205.11; 128/200.24; 128/203.25; 128/204.18; 128/203.12

(58) Field of Classification Search ............. 128/200.24, 128/203.12, 203.18, 203.22, 204.11, 204.12, 128/204.24–204.26, 205.24, 206.11, 207.18; 137/834, 26.3
See application file for complete search history.

(56) References Cited

U.S. PATENT DOCUMENTS

| | | | | |
|---|---|---|---|---|
| 4,430,994 A * | 2/1984 | Clawson et al. | ......... | 128/203.27 |
| 4,459,981 A * | 7/1984 | Mascher et al. | ......... | 128/202.26 |
| 5,062,774 A * | 11/1991 | Kramer et al. | ............. | 417/413.1 |
| 5,378,126 A * | 1/1995 | Abrahamson et al. | ........ | 417/479 |
| 5,549,105 A * | 8/1996 | Bloch et al. | ............. | 128/203.12 |
| 7,328,703 B1 * | 2/2008 | Tiep | ........................ | 128/207.18 |

FOREIGN PATENT DOCUMENTS

| EP | 266 964 A2 | 5/1988 |
|---|---|---|
| EP | 0806216 A1 | 11/1997 |

* cited by examiner

*Primary Examiner* — Annette Dixon
(74) *Attorney, Agent, or Firm* — McGlew and Tuttle, P.C.

(57) ABSTRACT

A device for supplying a respirator with breathing gas is designed in a modular design. To accomplish the object, a cover plate (9), a distributor plate (20) and a half shell body (11) are provided in a sandwich-like design, wherein said distributor plate (20) has walls (3, 5) projecting on both sides, which are connected to the cover plate (9) and to the half shell body (11) and define gas ducts (7) as well as a buffer volume (12).

19 Claims, 6 Drawing Sheets

DEVICE FOR SUPPLYING A RESPIRATOR WITH BREATHING GAS

CROSS REFERENCE TO RELATED APPLICATIONS

This application claims the benefit of priority under 35 U.S.C. §119 of German Patent Application DE 10 2008 057 180.6 filed Nov. 13, 2008, the entire contents of which are incorporated herein by reference.

FIELD OF THE INVENTION

The present invention pertains to a device for supplying a respirator with breathing gas.

BACKGROUND OF THE INVENTION

A device of this type is known from EP 266 964 A2. A distributor plate, which is provided for mounting pneumatic elements, is provided on the underside with groove-like recesses, which act as gas ducts. The gas ducts are closed against the environment by means of a closing plate, which is in contact with the underside by means of a flat packing. The distributor plate also contains a mixing and buffer volume, which is an integral part of the distributor plate. The closing plate is fastened to the distributor plate by means of screws. The prior-art distributor plate consists of aluminum and its manufacture is complicated. Due to manufacturing according to the diecasting method and because of an inhomogeneous cooling process and because of the great variations in wall thickness, dimensional imperfections may arise, which must be eliminated by finishing. Expensive finishing must be performed especially in the area of functional surfaces especially because of the poor surface finish of parts manufactured according to the diecasting process. In case of changes in parameters, for example, the mounting or additional components or the change in the volume of the integrated buffer volume, it is usually necessary to prepare a completely new manufacturing die.

SUMMARY OF THE INVENTION

The basic object of the present invention is to propose a device of the type which has a compact and modular design.

According to the invention, a device for supplying a respirator with breathing gas has a modular design. A cover plate module, a distributor plate module and a half shell body module are provided in a sandwich-like design. The distributor plate module has walls projecting on both sides, which are connected to the cover plate and to the half shell body and define gas ducts as well as a buffer volume.

The advantage of the present invention is essentially that a gas mixing block is built up of three basic components to supply a respirator with breathing gas, wherein a distributor plate with walls projecting on both sides, which define gas ducts, is fastened in a sandwich-like manner between a cover plate and a half shell body. The cover plate and the half shell body lie on the free ends of the walls. The sandwich design leads to good space utilization of the gas mixer block.

The distributor plate comprises a basic carrier, which has first walls on a first partial surface and a second wall on a second partial surface arranged opposite. The first walls extend, at least partly, e.g., in parallel to one another and define, together with the cover plate, individual gas ducts. The necessary cross-sectional area of the gas ducts can be set by varying the height of and the distance between the first walls, so that the gas ducts have an essentially rectangular cross section. The wall in the area of the second partial surface has a ring-shaped design and corresponds to the outer contour of the half shell body, which forms a mixing and buffer volume for the gas mixture together with the second wall. Thus, a basic carrier of an essentially plate-shaped design, which is provided with walls on both sides, is provided as the carrying component of the distributor plate. The walls stand vertically on the basic carrier and have essentially equal wall thickness over their course, and additional walls in the form of reinforcing walls may be present on both sides of the basic carrier. The free ends of the gas-carrying walls are connected either to the cover plate or to the half shell body. The volume of an enclosed buffer volume, for example, in the area of the half shell body, or the cross-sectional area of the gas ducts in the area of the cover plate can be varied and adapted to changed capacity specifications by varying the height of the walls, i.e., the distance of the free ends of the walls relative to the base plate.

The distributor plate, cover plate and half shell body advantageously consist of an electrically conductive, e.g., thermoplastic plastic and are welded to one another by means of a laser beam process. Due to the components being welded to one another, cost-effective manufacture is obtained along with high strength in the area of the weld seams. The connection is gas-tight and the use of an additional seal is therefore no longer necessary. The cover plate, distributor plate and half shell body can be manufactured in an especially simple manner according to the injection molding process. Finishing of the functional surfaces is reduced to a minimum due to manufacture according to the plastic injection molding process. A pressure of up to 10 bar may occur within the gas ducts defined by the first walls, while the internal pressure is usually limited to a lower pressure in the mixing and buffer volume, which contains the metered gas mixture. The sandwich design of the gas mixer block also leads to a compact design, which can be integrated into existing device housings in a simple manner. Flow resistances in the form of orifices or sintered bodies are advantageously integrated in the gas ducts in order to make it possible to measure gas flows based on the pressure loss. The pressure difference can be measured by means of measuring holes in front of and behind the flow resistances. The functional components needed for metering the gas, such as valves, measuring transducers as well as the connection flanges for supplying the pressurized gases to be metered, may be fastened directly to the cover plate or second partial surface of the basic carrier. Due to the use of both the cover plate and the second partial surface of the basic carrier for fastening the components, a large number of valves or measuring transducers can be fastened without any flexible tube connections being needed.

An exemplary embodiment of the present invention is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
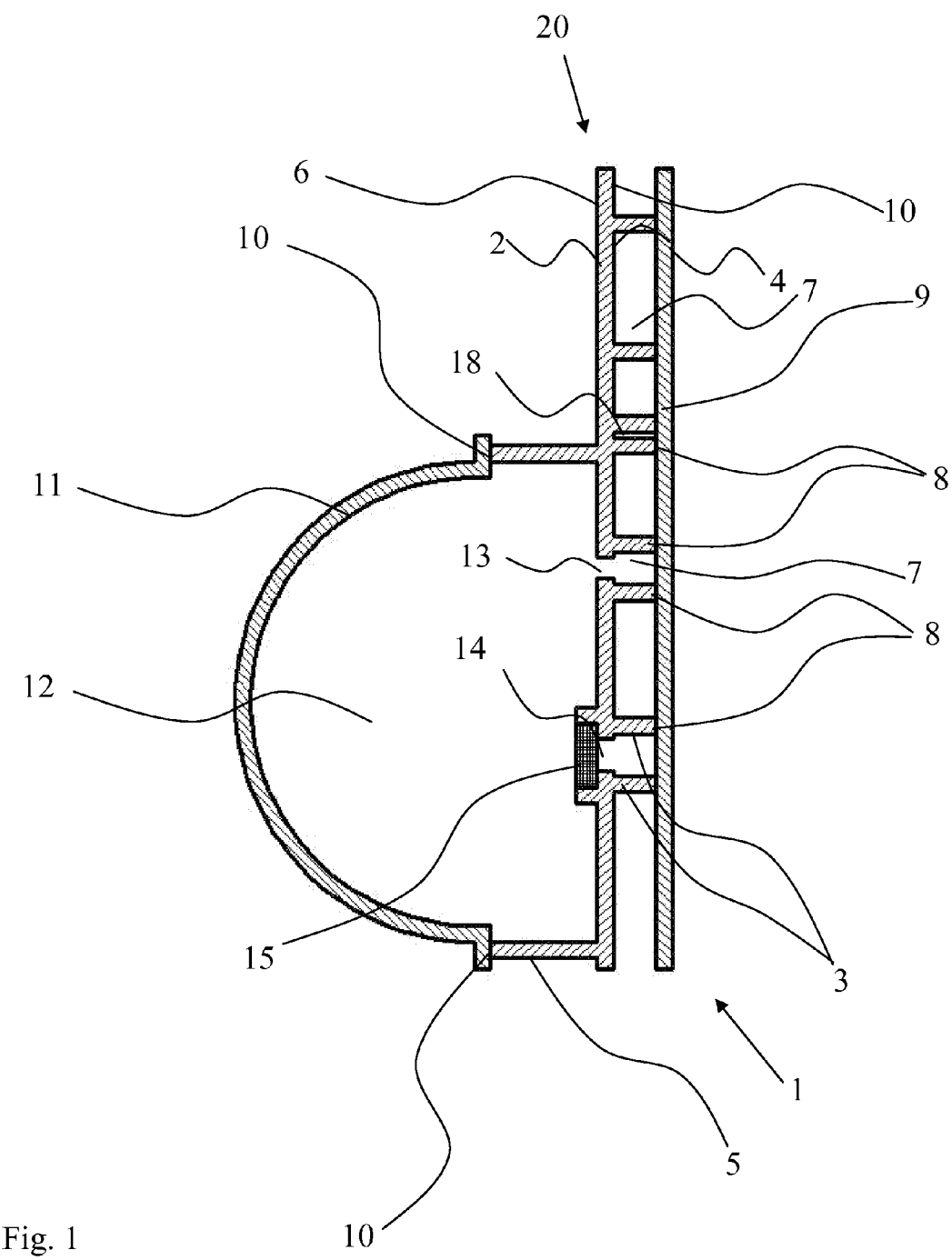
FIG. 1 is a sectional view of a gas mixer block.

Referring to the drawings in particular, FIG. 1 schematically shows the design of a gas mixer block 1 for supplying a patient with breathing gas. The gas mixer block 1 comprises a distributor plate 20 with a basic carrier 2 and first walls 3 extending in parallel to one another on a first partial surface 4 and a second wall 5 on a second partial surface 6 of the basic carrier 2. Rectangular gas ducts 7 are defined by the first walls 3 in the area of the first partial surface 4 of the basic carrier 2. The free ends 8 of the first walls 3 are welded to a cover plate 9 and the gas ducts 7 are thus sealed against the environment. The gas ducts 7 are designed such that the necessary cross sectional area is set by selecting the height of the walls, and the surface of the gas ducts 7 covered by the cover plate 9 is kept as small as possible for reasons of strength. The second wall 5 has an annular design in the area of the second partial surface 6, and the free end of this wall is connected to a half shell body 11. The second wall 5 and the half shell body 11 define a mixing and buffer volume 12, which is used as a mixing chamber and storage unit for the fresh gas to be delivered. The mixing and buffer volume 12 is connected to the gas ducts 7 via flow ducts 13, 14. The flow duct 14 additionally also contains a sintered body 15 as a flow resistance in order to determine the gas volume flow flowing out of the mixing and buffer volume 12 by means of a differential pressure transducer, which determines the pressure drop over the sintered body 15.

Figure 2:
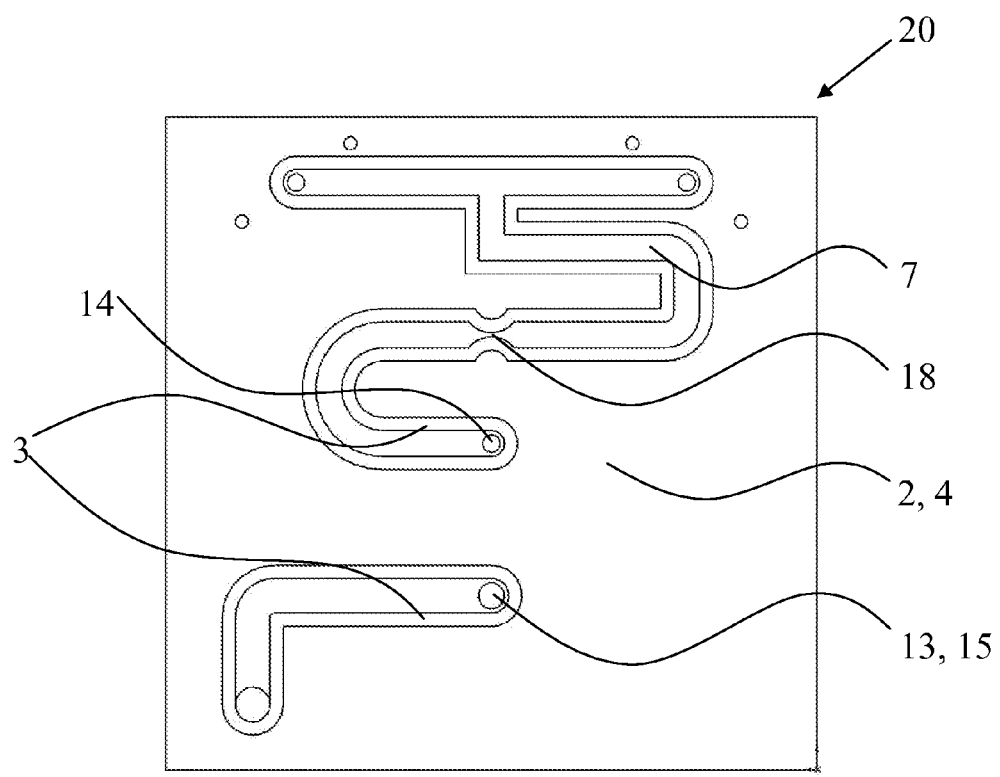
FIG. 2 is a top view of a first partial surface of the distributor plate.

FIG. 2 shows a top view of the first partial surface 4 of the distributor plate 20 with a plurality of first walls 3, which define gas ducts 7. Defined cross-sectional contractions 18 are provided as flow resistances for flow measurement by means of differential pressure sensing within predetermined gas ducts 7.

Figure 3:
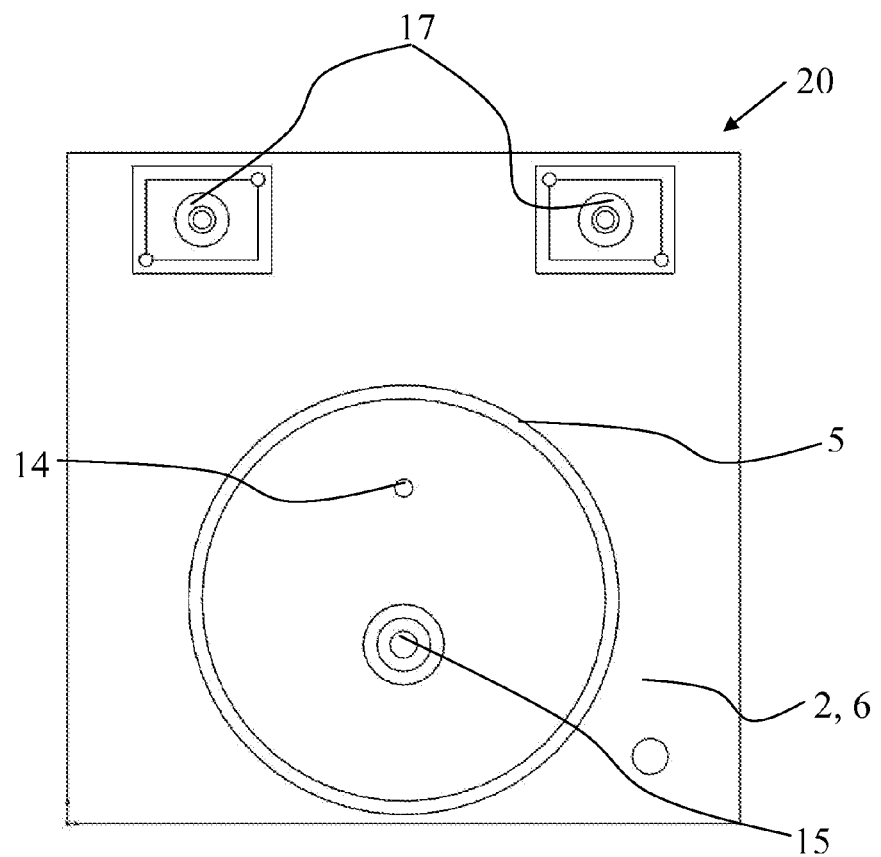
FIG. 3 is a top view of a second partial surface of the distributor plate.

FIG. 3 shows a top view of the second partial surface 6 of the distributor plate 20 with the second wall 5 extending in a ring-shaped pattern. Connection flanges 17 for pressurized gas ports, not shown in greater detail, with which pressurized gases, for example, oxygen, compressed air or laughing gas, are fed into predetermined gas ducts 7, FIG. 1, in order to be mixed in the mixing and buffer volume 12 to obtain the desired breathing gas composition, are located on the top side of the basic carrier 2 in the area of the second partial surface 6.

Figure 4:
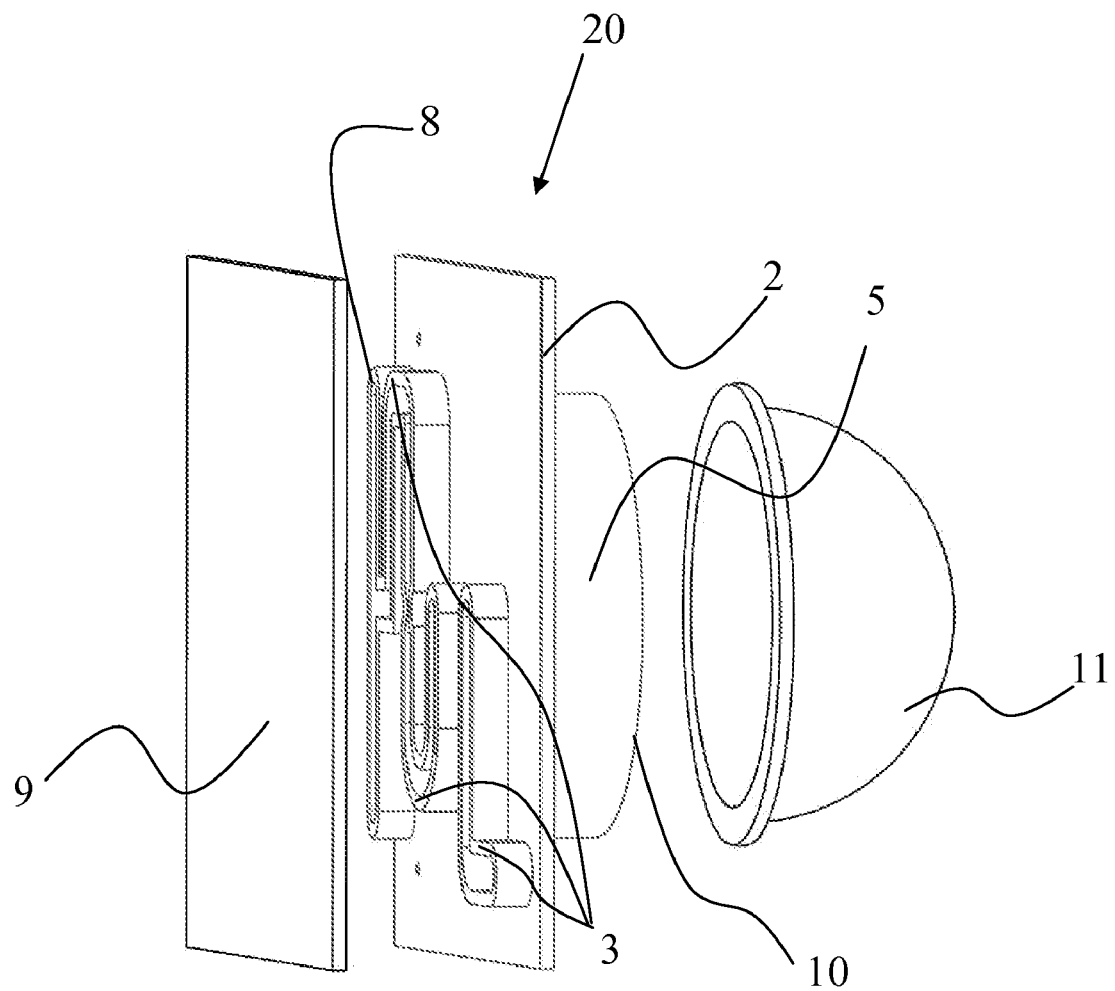
FIG. 4 is a perspective view of the gas mixer block.

FIG. 4 shows the components of the gas mixer block 1, the cover plate 9, the distributor plate 20 and the half shell body 11 in a perspective view. The cover plate 9, distributor plate 20 and half shell body 11 consist of an electrically conductive, thermoplastic plastic, which can be welded by means of the laser beam process. The weld seams are located between the free ends 8 of the first walls 3 and the cover plate 9 and the free ends 10 of the second wall 5 and the half shell body 11. The plastic is provided with a filler, which makes it electrostatically conductive. The dry gases flowing through the gas mixer block 1 are prevented hereby from bringing about electrostatic charging of the gas mixer block due to friction on the surfaces.

Figure 5:
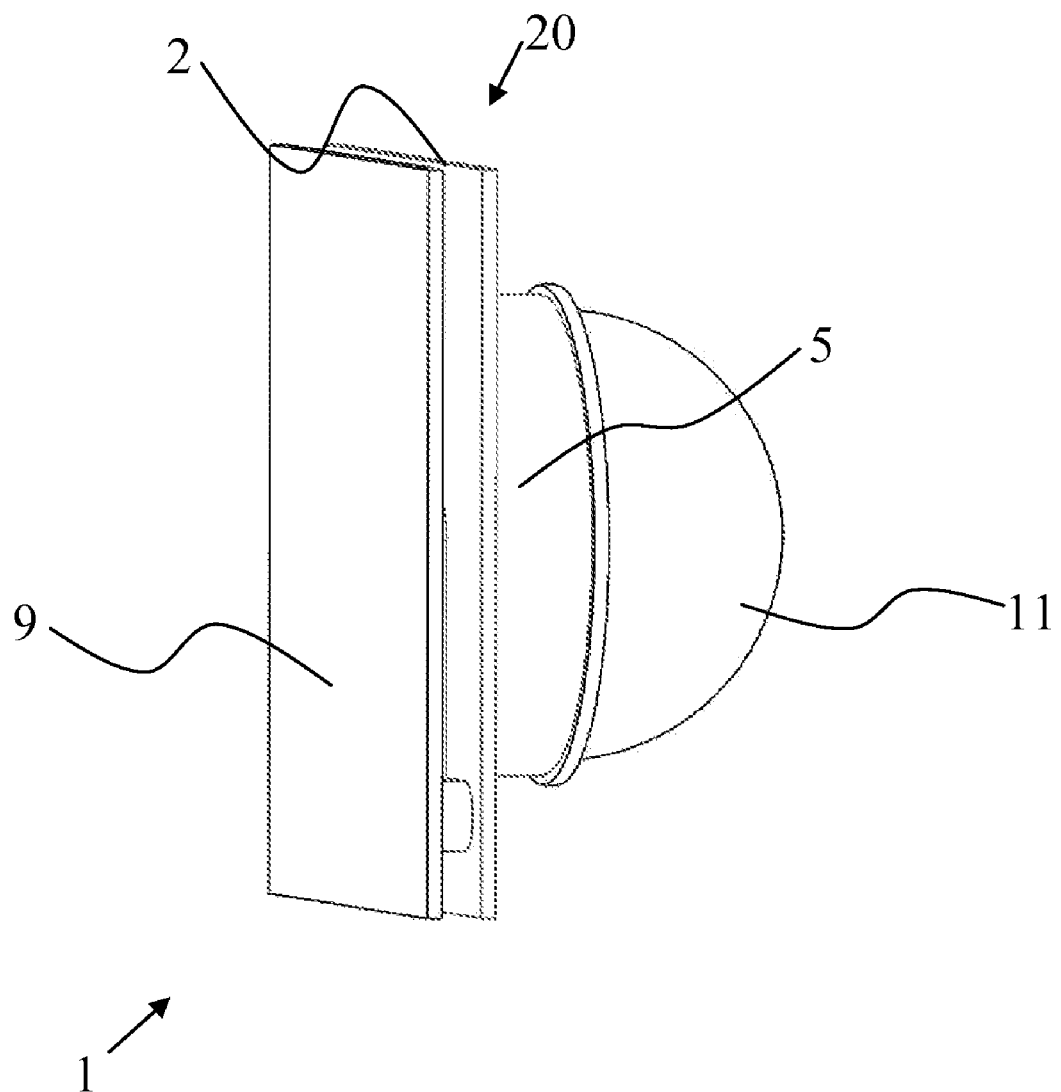
FIG. 5 is the gas mixer block according to FIG. 4 with welded-on partial components.
Figure 6:
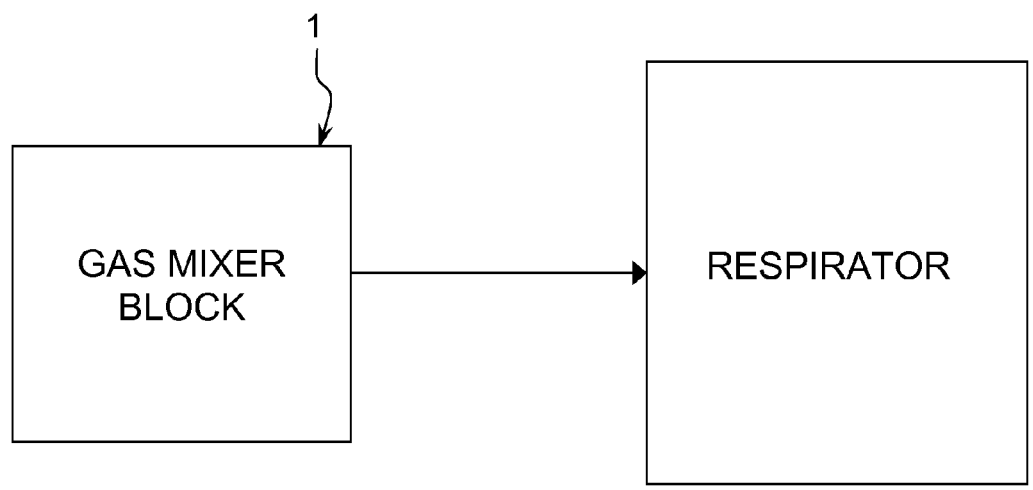
FIG. 6 is a schematic view showing a gas mixer block supplying a respirator.

FIG. 5 shows the gas mixer block 1 after welding the partial components.

While specific embodiments of the invention have been shown and described in detail to illustrate the application of the principles of the invention, it will be understood that the invention may be embodied otherwise without departing from such principles.

What is claimed is:

1. A device for supplying a respirator with breathing gas, the device comprising:
    a half shell body with a half shell free end;
    a cover plate;
    a distributor plate with a basic carrier with a first side and a second side, said basic carrier having walls including first side walls arranged projecting from said first side of said basic carrier to first side wall free ends and a second side wall arranged projecting from said second side of said basic carrier to a second side wall free end, said distributor plate being arranged in a sandwich manner between said half shell body and said cover plate, wherein said first side walls arranged projecting from said first side extend in parallel to one another at least in some sections and said first side free ends contact an inner surface of said cover plate to form gas or flow ducts defined by said first side, said first side walls and said inner surface of said cover plate and said second side wall arranged projecting from said second side follows a contour of said half shell body and said second side wall free end contacts said half shell free end of said half shell body to define a mixing and buffer volume.

2. A device in accordance with claim 1, wherein the distributor plate, half shell body and cover plate consist of a plastic and are connected to one another by at least one of welding and bonding in an area of the free ends of the walls to provide a connection that is gas-tight.

3. A device in accordance with claim 1, further comprising connection flanges wherein the distributor plate is provided with said connection flanges for pressurized gas ports on the second partial surface facing said half shell body.

4. A device in accordance with claim 1, wherein said gas or flow ducts have one or more changes in wall spacing to define one or more flow resistances for carrying out pressure or flow measurements.

5. A device in accordance with claim 1, wherein at least partial components consist of an electrically conductive material.

6. A device for supplying a respirator with breathing gas, the device comprising:
    a half shell body module;
    a cover plate module;
    a distributor plate module with a basic carrier with a half shell body side and a cover plate side, said basic carrier having walls projecting from said cover plate side of said basic carrier to wall end faces and a wall projecting from said half shell body side to a wall end face, said distributor plate being sandwiched between said half shell body and said cover plate with said wall end faces of said cover plate side walls in contact with said cover plate module and said wall end face of said half shell body wall in contact with said half shell body module, wherein said cover plate side walls form gas or flow ducts and said half shell body wall follows a contour of said half shell body to cooperate with said half shell body module to form a buffer volume.

7. A device in accordance with claim 6, wherein the distributor plate module, half shell body module and cover plate module consist of a plastic and are connected to one another by at least one of welding and bonding in an area of free ends of the walls.

8. A device in accordance with claim 6, further comprising connection flanges wherein the distributor plate module is provided with said connection flanges for pressurized gas ports on the half shell body side facing said half shell body.

9. A device in accordance with claim 6, wherein said gas or flow ducts have one or more flow resistances for carrying out pressure or flow measurements.

10. A device in accordance with claim 6, wherein at least partial components consist of an electrically conductive material.

11. A device for supplying a respirator with breathing gas, the device comprising:
 a half shell body with a half shell free end surface lying in a half shell end plane;
 a cover plate with a flat contact surface;
 a distributor plate comprising a half shell body side and a cover plate side, said distributor plate having integrally formed first walls projecting from said cover plate side to first wall end faces lying in a first wall end face plane and a second wall projecting from said half shell body side to a second wall end face lying in a second wall end face plane, said second wall having a second wall contour corresponding to a contour of said half shell free end surface, said cover plate flat contact surface being in contact with and fixed to said first wall end faces to form gas flow ducts defined by portions of said cover plate side between adjacent first side walls, said first side walls and portions of said flat contact surface of said cover plate, said half shell free end surface being in contact with and fixed to said second wall end face to form a mixing and buffer volume defined by an inner surface of said half shell body and an inner surface of said second side wall.

12. A device in accordance with claim 11, wherein:
 said distributor plate, said half shell body and said cover plate are formed as injection molded parts of a plastic material.

13. A device in accordance with claim 12, wherein:
 said cover plate flat contact surface is fixed to said first wall end faces by at least one of welding and bonding to provide a connection that is gas-tight; and
 said half shell free end surface is fixed to said second wall end face by at least one of welding and bonding to provide a connection that is gas-tight.

14. A device in accordance with claim 13, wherein said half shell body, said cover plate and said distributor plate each comprise an electrically conductive material.

15. A device in accordance with claim 14, wherein said gas or flow ducts have one or more changes in wall spacing to define one or more flow resistances for carrying out pressure or flow measurements.

16. A device in accordance with claim 13, wherein at least a portion of each of said half shell body, said cover plate and said distributor plat consists of an electrically conductive material.

17. A device in accordance with claim 13, further comprising connection flanges wherein the distributor plate module is integrally formed with said connection flanges for pressurized gas ports on the half shell body side facing said half shell body.

18. A device in accordance with claim 12, wherein said gas or flow ducts have one or more changes in wall spacing to define one or more flow resistances for carrying out pressure or flow measurements.

19. A device in accordance with claim 11, wherein said gas or flow ducts have one or more changes in wall spacing to define one or more flow resistances for carrying out pressure or flow measurements.

* * * * *